Figure 1:
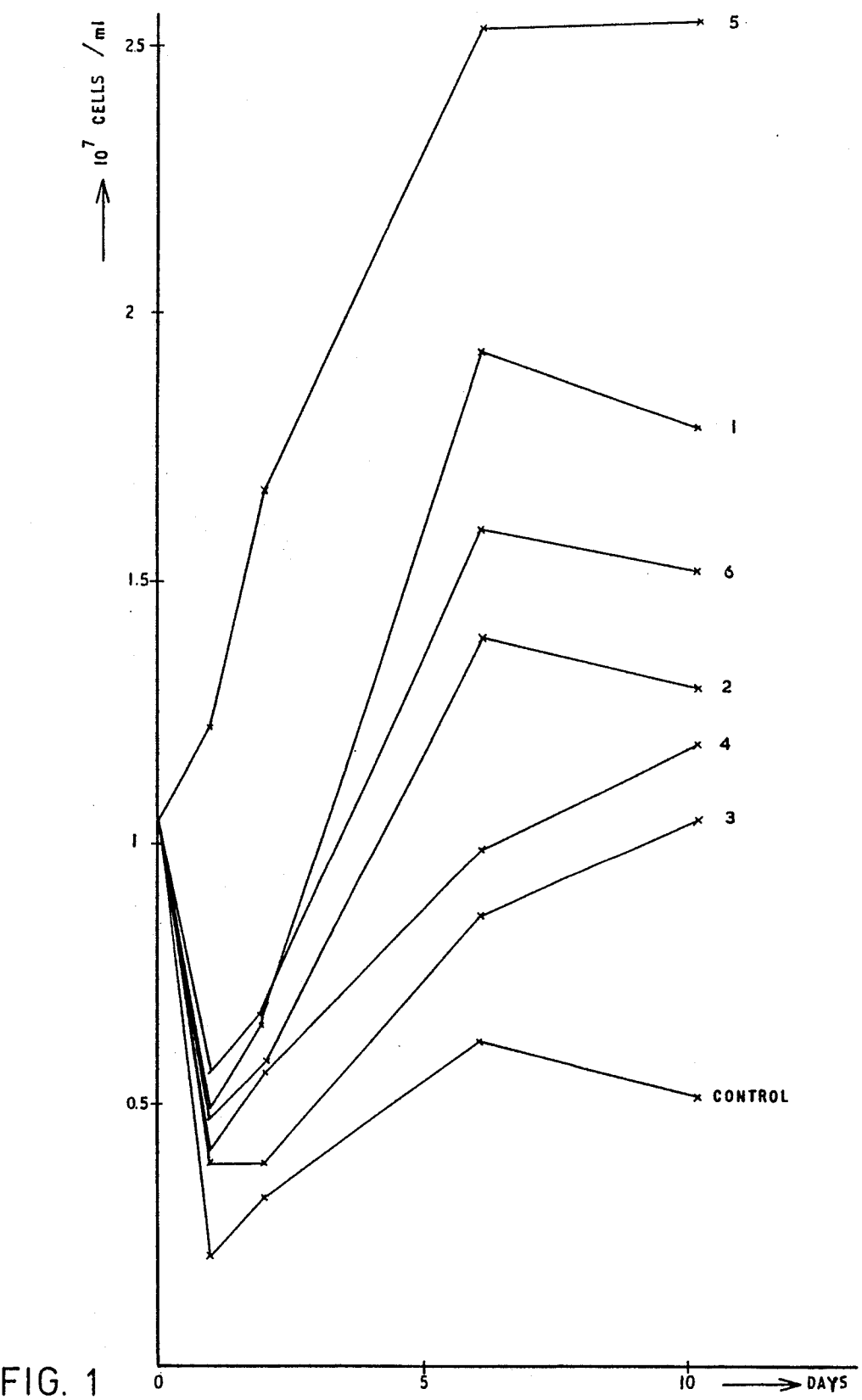

United States Patent [19]

Schäfer et al.

[11] Patent Number: 4,818,440
[45] Date of Patent: Apr. 4, 1989

[54] NOVEL POLYETHER CARBOXYLIC ACID DERIVATIVES, AS WELL AS THEIR USES

[75] Inventors: Werner Schäfer, Oberwil; Rolf Schäfer; Doris Schäfer, both of Arisdorf, all of Switzerland; Johan G. Aalbers, As Bodegraven; Jacob K. Smid, Sx Bodegraven, both of Netherlands

[73] Assignee: Stamicarbon B.V., Bodegraven, Netherlands

[21] Appl. No.: 523,781

[22] Filed: Aug. 16, 1983

[30] Foreign Application Priority Data

Aug. 19, 1982 [NL] Netherlands ............... 8203257

[51] Int. Cl.$^4$ ............... A61K 7/50; C07C 103/50; C11D 1/10; C11D 17/08
[52] U.S. Cl. ............... 252/546; 252/153; 252/DIG. 5; 252/DIG. 13; 260/404; 424/70; 514/563; 514/844; 514/847; 514/881; 562/567
[58] Field of Search ............ 260/404; 562/567, 553; 252/527, 546, 153, DIG. 5, DIG. 13; 424/70; 514/563, 844, 847, 873, 881

[56] References Cited

U.S. PATENT DOCUMENTS

| | | | |
|---|---|---|---|
| 2,183,853 | 12/1939 | Haussmann | 260/404 |
| 3,072,690 | 1/1963 | Lee | 260/404.5 |
| 3,941,710 | 3/1976 | Gilbert | 252/99 |
| 3,959,460 | 5/1976 | Vanlergerghe | 424/70 |
| 3,990,991 | 11/1976 | Gerstein | 252/542 |
| 4,122,043 | 10/1978 | Kersnar | 252/527 |
| 4,130,497 | 12/1978 | Oneto | 252/545 |
| 4,242,215 | 12/1980 | Smid | 252/100 |
| 4,374,056 | 2/1983 | Watanabe | 252/546 |
| 4,443,362 | 4/1984 | Guth | 252/545 |

FOREIGN PATENT DOCUMENTS 1169496  11/1969  United Kingdom .

OTHER PUBLICATIONS

*McCutcheon's Detergents & Emulsifiers-1978 North American Edition,* published by MC Publishing Co., 175 Rock Rd., Glen Rock, N.J. 07452, pp. 168, 179, 227 and 239.

AKPO surfactant bulletin published by CHEM-Y, Bodegraven, Holland, 4 pp. (publication date uncertain).

*Primary Examiner*—Dennis Albrecht
*Attorney, Agent, or Firm*—Browdy & Neimark

[57] ABSTRACT

Novel surfactant compounds are provided of the formula $R-CO-NH-(C_2H_4O)_n-CH_2COOH$, wherein R—CO— is the residue of at least one aliphatic carboxylic acid of 6-22 carbon atoms and n represents a number having an average of 2-10, as well as their salts with alkali metals, ammonium and amines. These compounds possess not only a low primary toxicity, but also a low secondary toxicity for the skin, and accordingly they are especially useful in cosmetic compositions, compositions for non-automatic dishwashing and laundering compositions for the fine laundry.

13 Claims, 2 Drawing Sheets

NOVEL POLYETHER CARBOXYLIC ACID DERIVATIVES, AS WELL AS THEIR USES

This invention relates to novel polyether carboxylic acid derivatives and their uses.

Polyether carboxylic acids of the formula R—X—(CH$_2$—CH$_2$—O)$_n$—CH$_2$—COOH, where R is a hydrophobic residue, X is oxygen or in some cases sulfur and n is a number having a value which in general is not over 10, are already known for a long time and are used in actual practice for over 25 years. Among these compounds those in which n has an average value of about 1 are only useful as emulsifiers, whereas compounds, wherein n has an average value of 2 or higher have a much wider use as detergents for several purposes.

A first mentioning of this class of compounds and of the preparation of compounds, wherein X is oxygen, can be found in U.S. Pat. No. 2,183,853. In the right column on page 1 of this patent a large number of formulae has been given of possible compounds which according to that patent would be useful for the same purposes. Among them are also compounds of the formula R—CO—NH—(CH$_2$—CH$_2$—O)$_2$—CH$_2$—COOH, wherein R is an aliphatic, cycloaliphatic or mixed aromatic-aliphatic residue of more than 8 carbon atoms. However, it does not appear from this U.S. patent, that such a compound ever was prepared actually. In as far as is known to the present applicant who is active in this field already for many years, this neither has been the case later on and these facts have been further confirmed by a search of the patent literature and of Chemical Abstracts, partially carried out through computer programs, and going back until 1967. Consequently, the fact that U.S. Pat. No. 2,183,853 states about the entire group of compounds that they would be suitable as surfactants for various purposes, has not constituted an instigation to prepare this specific kind of compounds and to examine them further. Possibly, the cause thereof should be seen therein that the group of compounds of the formula R—O—(CH$_2$—CH$_2$—O)$_n$—CH$_2$—COOH and their salts are quite satisfying for various purposes and as such are neither damaging to the skin. For these reasons these known ether carboxylic acids are used a.o. for cosmetic purposes.

As regards the influence of a surfactant on the skin, it is in particular the toxicity to the bacterial flora on the skin which is of importance. In this respect a primary and a secondary toxicity can be noted. The primary toxicity is the one which is caused by the surfactants themselves. The secondary toxicity is the toxicity of the decomposition products of the surfactant which are formed on degradation thereof by the bacterial skin flora. Until recently this secondary toxicity was hardly taken into consideration, but of course it is of importance for the skin tolerance of a surfactant.

The known polyether carboxylic acids of the type R—O—(C$_2$H$_4$O)$_n$—CH$_2$COOH and their salts are satisfactory as regards their primary toxicity, but as has appeared now, they possess a relatively considerable secondary toxicity. Surprisingly, it has now been found that compounds of the formula R—CO—NH—(C$_2$H$_4$O)$_n$—CH$_2$—COOH, wherein R—CO— is the residue of one or more aliphatic carboxylic acids of 6-22 carbon atoms, n is a number having an average value of 2-10, as well as their salts, are detergents which not only possess a low primary toxicity, but also a low secondary toxicity.

As appears from the above, these compounds have never been prepared before and accordingly they are novel compounds.

It should be remarked that compounds of the formula R—CO—NH—CH$_2$—CH$_2$—O—CH$_2$COOX, wherein R is an aliphatic, cycloaliphatic or alkyl-aromatic hydrocarbon residue of 7-21 carbon atoms and X is hydrogen, Na, K, NH$_4$ or the cation of an organic ammonium base, have been disclosed in the abandoned German patent application No. 2644498.4 (Offenlegungsschrift No. 2644498), wherein it has been proposed to use such compounds in detergents as complete or partial replacement of the polyphosphate. Consequently, it concerns here compounds of the present kind, wherein, however, n=1. Compounds having such a low n value are only useful as emulsifiers. However, the compounds of the present invention are detergents, and although a compound of a lower n value, such as disclosed in the above-mentioned Offenlegungsschrift can be used in some of the compositions of the invention, it should then always be used in conjunction with a real detergent, i.e. a compound of the same type but having a higher value of n.

The present invention, accordingly, provides the above defined novel compounds.

The carbon chain of the aliphatic acid residue may be either straight or branched and may contain a saturated carbocyclic or heterocyclic ring in the chain. Furthermore, the chain may be saturated or unsaturated. If R—CO— is derived from natural fats or oils, this residue in fact is a mixture of several acid residues.

The present compounds can be prepared simply by reacting a product of the formula R—CO—NH—(C$_2$H$_4$O)$_n$H in alkaline medium with a salt of a haloacetic acid, usually with sodium chloroacetate, as is known per se for the preparation of the usual polyether carboxylic acids. The present compounds can be prepared in the form of the free acids or in the form of alkali metal, alkaline earth metal, ammonium or amine salts.

The starting product for this reaction can be prepared in turn by reacting a suitable acid amide or mixture of acid amides with ethylene oxide. In all these cases addition only occurs to a single hydrogen atom of the amide; if more than one mole of ethylene oxide is used, each following molecule will add only to the already introduced terminal hydroxy group. Instead of the unmodified carbon amide, one may also start from a monoethanolamide. In this way a known product, wherein n=1, may be prepared directly by reacting the monoethanolamide with the monohaloacetic salt; the products of the present invention are prepared by first adding a further amount of ethylene oxide to this monoethanolamide, followed by the reaction with monohaloacetic salt. Ethanolamides of some fatty acids are commercial products so that sometimes it may be preferred to start from these commercial products, when preparing the present compounds. However, in the case of fatty acid mixtures obtained from oils or fats, one will generally start from the unmodified amide.

Due to their good surfactant properties and particularly favorable primary and secondary toxicity values, the present compounds are particularly suitable for use as detergents and the like in cometic compositions, such as shampoos, bubble baths and creams, in liquid soaps for household purposes, in dish-washing agents, particularly for hand-washing, and in laundering compositions for the fine laundry. Consequently, this invention also relates to these uses and to such agents and compositions.

The testing of surfactants for the secondary toxicity on skin bacteria is carried out as follows:

The skin bacteria are cultures at a temperature of 33° C. (the optimum) in a medium containing sufficient nutrients until a concentration of $10^7$ cells per ml has been obtained. Thereafter the cells are washed and transferred to a medium which contains all the necessary nutrients, including the spore elements, however with the exception of carbon. To this mixture 0.05% by weight of the surfactant to be tested is added and the development of the number of cells with the time is measured. A control test is carried out with the same nutrient mixture, but without any carbon addition.

Because the bacteria previously have been cultured in a nutrient-rich medium, they need some time to get accustomed to the new medium, which leads to an intial decrease of the number of cells during the first days. Thereafter, this decrease will continued, if the added surfactant has a high secondary toxicity. If, however, the secondary toxicity is low, the number of bacteria will increase again. After a further number of days the number of cells will start to decrease for the second time, but this time because the carbon source has been depleted.

The above is illustrated by the enclosed FIG. 1 which shows the number of cells for six compounds of the present invention and a control. Curves 1-4 have been obtained using compound $C_{17}H_{35}CO-NH(C_2H_4O)_nCH_2COONa$, wherein in the products 1-4 n=3, 4, 5 and 6 respectively; curve 5 has been obtained with the compound $C_{17}H_{35}CONHCH_2CH_2OCH_2COONa$ and curve 6 with the compound $C_{17}H_{35}CO-NH(C_2H_4O)_6CH_2COONa$. It appears from these curves that all the tested compounds can be utilized as carbon sources by the bacteria, though in varying degrees.

Figure 2:
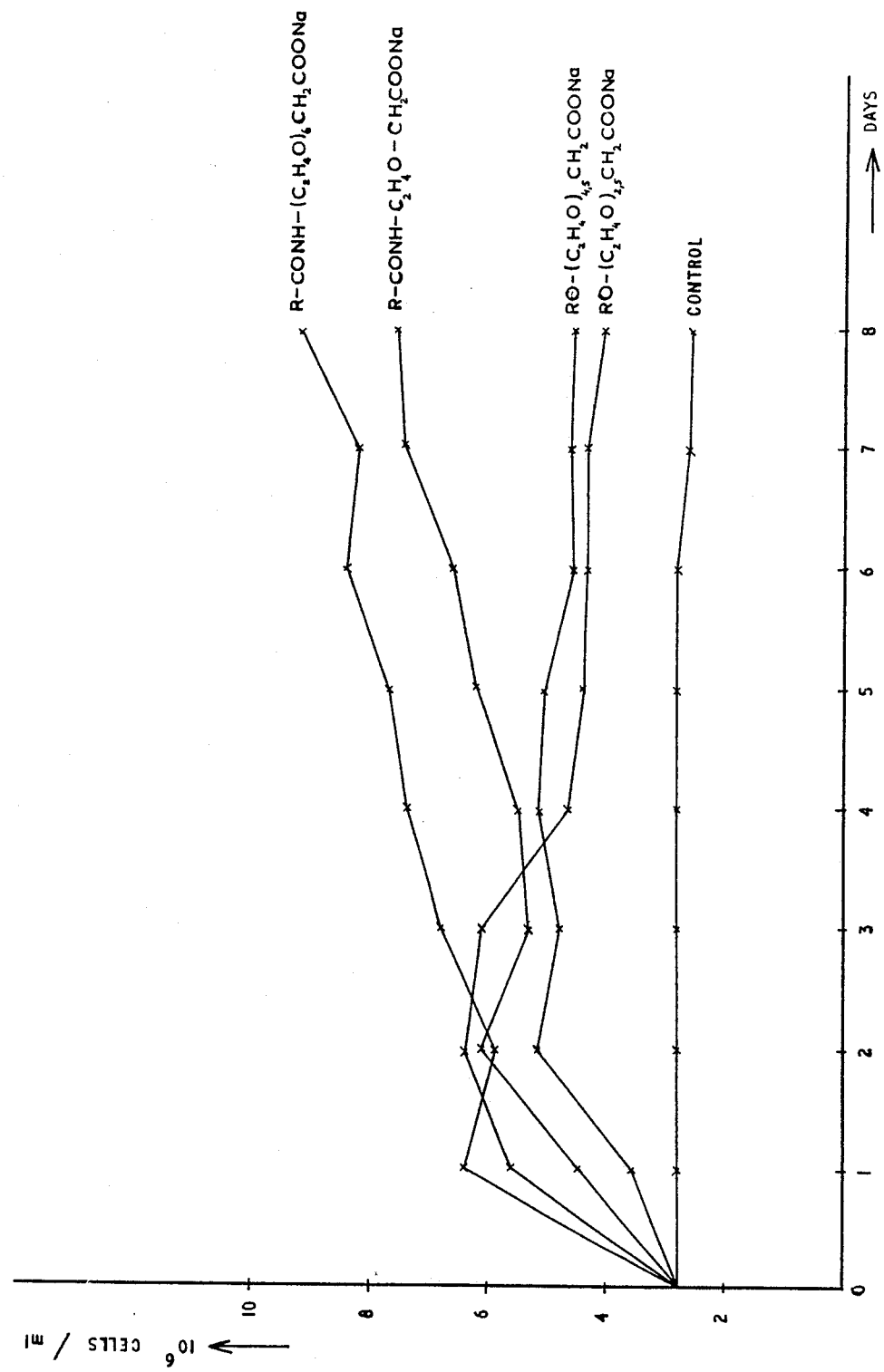

FIG. 2 shows a graph in which the time starts after the original decrease in the number of cells, in this case to about $2.5 \cdot 10^6$/ml. In this case the compounds $RCO-NH(C_2H_4O)_nCH_2COONa$, wherein RCO was derived from coco fatty acids, and wherein n was 1 and 6 respectively, were compared with a control and with two known ether carboxylic acid salts of the formula $RO-(C_2H_4O)_nCH_2COONa$, wherein in both cases R was derived from a natural mixture of lauryl and myristyl alcohols (lauryl:myristyl=70:30) and n in one case was 4.5 and in the other case was 2.5. As is clear from this graph, the novel products of the present invention are clearly superior over these known products.

The invention is illustrated hereinafter with some examples of the preparation of the novel compounds and of formulations in which they are used. However, these examples are for illustrative purposes only and do not limit the invetion in any way.

EXAMPLE 1

Preparation of
$C_{11}H_{23}-CO-NH-(C_2H_4O)_6-CH_2COOH$ (a) 1000 moles (243 kg) of the monoethanolamide of lauric acid in the form of the commercial product "Rewoamid L203" is reacted with 5000 moles (220 kg) of epoxyethane in the presence of 0.5 kg of sodium methylate as a catalyst. The reaction is carried out at 110°-130° C. in an autoclave under a pressure of 196-294 kPa. The reaction time is about ½ to 1 hour. The yield is quantitative.

(b) The product of step (a) is reacted with a molar excess of sodium monochloro acetate (175 kg) and 60 kg of powdery NaOH. The monochloro acetate is added in 6 portions and the NaOH in 12 portions. The reaction temperature is 60°-65° C.; the addition time is 6 hours, whereafter the reaction mixture is left standing at this temperature for one more hour. The conversion of the polyetheralcohol to the polyetheracetate is about 75 to 80%.

The so obtained crude product is purified by adding 183 kg of 30% HCl to 702 kg deionized water, heating the mixture and adding the crude reaction mixture of the foregoing step. The entire mixture is heated at 90° C. and an oil separates. This oil is the desired carboxylic acid which is obtained in a yield of 396 kg. The product is initially liquid, but after standing some time it becomes solid, whereafter it can be molten and resolidified again.

EXAMPLE 2

Preparation of
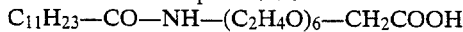
$C_{17}H_{35}CO-NH-(C_2H_4O)_8-CH_2COOH$

The commercial monoethanolamide of stearic acid (Rewoamid S280) (1 mole) is reacted with 7 moles of epoxyethane in the presence of 0.6 kg sodium methylate (80%). The reaction is carried out in an autoclave like in Example 1 and the reaction time is about ½ hour. Thereafter, the product is reacted with about 1.5 moles of sodium monochloro acetate and about 1.5 moles of powdery NaOH. The reaction temperature is 60°-65° C.; the monochloro acetate is added in 6 portions and the NaOH in 12 portions.

The total addition time is 6 hours, whereafter the reaction mixture is left standing for another hour. The conversion is about 80-85%. From the so obtained crude product the acid is liberated by heating with the same weight amount of about 7% HCl. The product is obtained as a liquid which solidifies after some time and which can be melted and resolidified again.

EXAMPLE 3

Shampoo or Shower Composition

| | |
|---|---|
| $C_{11}H_{23}-CO-NH-(C_2H_4O)_3-CH_2COOH$ | 20.8% |
| NaOH | 2.2% |
| Water | 77.0% |

Perfume and dye in small amounts to obtain acceptable odor and color. The pH of the so obtained mixture is 7.4. The composition is neutralized with 37% HCl to pH=4.2 $\eta^{20}$=1400 mPa·s.

EXAMPLE 4

Shampoo or Showering Composition

| | |
|---|---|
| $C_{11}H_{23}-CO-NH-(C_2H_4O)_3-CH_2COONa$ | 3% |
| 28% ethersulfate of the formula $RO-(C_2H_4O)_2SO_3Na$[1] | 25% |
| Water | 69.2% |
| NaCl | 2.8% |

[1]This product was derived from a commercial alcohol, Dobanol, which is a mixture of $C_{12}$ and $C_{13}$ alcohols of which a part possesses a branched chain.

Perfume and dye as needed. $\eta^{20}$=2000 mPa·s.

EXAMPLE 5

Shampoo

| | Parts by weight |
|---|---|
| $C_{11}H_{23}-CO-NH-(C_2H_4O)_6-CH_2COOH$ | 12 |
| Coco fatty acid-diethyanolamide | 5 |
| Sodium laurylsulfate (30%) | 15 |
| Polyoxyethylated lanoline alcohol (16 oxyethylene units) | 5 |
| Water | to 100 |
| Triethanolamine | q.s. |

Preparation: The first four ingredients are stirred in water in the sequence mentioned above, and the pH of the mixture is then brought to a value of 6.5 with triethanolamine. Of course, perfume and dye can be added as needed.

EXAMPLE 6

Professional Shampoo

| | Parts by weight |
|---|---|
| $C_{11}H_{23}-CONH-(C_2H_4O)_4-CH_2COOH$ | 10 |
| 29% $RO-(C_2H_4O)_2SO_3Na$ (same product as in Example 4) | 25 |
| Diethanolamide of coco fatty acid | 7 |
| Fatty alcohol $(C_{12-14})$-polyglycolether (9EO)[a] | 10 |
| 1,3-Butyleneglycol | 3 |
| Isopropanol | 5 |
| Water | to 100 |
| Monoethanolamine | q.s. |

[a] EO means oxyethylene unit.

Preparation: The first six ingredients are stirred in water in indicated sequence and then the pH is adjusted at 6.8 with monoethanolamine.

The so obtained concentrated product is diluted for use with 0.5–5 parts by weight of water, as needed.

EXAMPLE 7

Baby Shampoo

| | Parts by weight |
|---|---|
| $C_{11}H_{23}CO-NH(EO)_5-CH_2COOH$ | 20 |
| Sarcosinate of coco fatty acid | 5 |
| Diethanolamide of coco fatty acid | 5 |
| Powdery protein hydrolysate (collagen) | 6 |
| Water | to 100 |
| Monoethanolamine | q.s. |

Preparation: The protein hydrolysate is dissolved in water, thereafter the remaining components are stirred into the solution and the pH is adjusted at 7.2 with monoethanolamine.

EXAMPLE 8

Protein Shampoo

| | Parts by weight |
|---|---|
| $C_{11}H_{23}-CONH-(EO)_6-CH_2-COOH$ | 20 |
| Fatty alcohol-polyglycolether-phosphate, sodium salt | 5 |
| Protein hydrolysate, powdery | 6 |
| Polyoxyethylated lanoline alcohol (24 EO) | 5 |
| Water | to 100 |
| 10 n aqueous sodium hydroxide | q.s. |

Preparation: The protein hydrolysate is added to water and when a clear solution has been obtained, the remaining components are stirred into the solution in the indicated sequence; finally the pH is adjusted to 5.5 with the aqueous sodium hydroxide.

EXAMPLE 9

Anti-dandruff Shampoo

| | Parts by weight |
|---|---|
| $C_{11}H_{23}-CONH-(EO)_6-CH_2COOH$ | 12 |
| undecyleneamide-4EO-$CH_2COOH$ | 3 |
| Fatty acid alkylolamide-sulfosuccinate (30%) | 12 |
| Diethanolamide of oleic acid | 5 |
| Polyoxyethylated lanoline alcohol (16 EO) | 6 |
| Fatty acid-protein condensate (40%) | 8 |
| Zinc-pyrithione (48%) | 1.5 |
| Water | to 100 |
| Monoethanolamine | q.s. |

Preparation: The products are stirred into water in the indicated sequence and finally the pH is adjusted to 6.8 with monoethanolamine. In het above examples of course perfume and/or dye can be added, also in as far as this has not been mentioned explicitly. The same is true for the compositions of the following examples.

EXAMPLE 10

Bubble Bath

| | Parts by weight |
|---|---|
| $C_{11}H_{23}-CONH-(EO)_6-CH_2-COOH$ | 10 |
| $RO-(C_2H_4O)_2SO_3Na$ (28%; same product as in Example 4) | 10 |
| Diethanolamide of lauric acid | 5 |
| Myristyl-cetyl-dimethylamine-oxide | 5 |
| Melissa oil | 2 |
| 1,3-Butyleneglycol | 6 |
| Water | to 100 |
| 10 n aqueous sodiumhydroxide | q.s. |

Preparation: The first four ingredients are stirred into water in the indicated sequence; butyleneglycol is added and then the pH is adjusted to 6.9 with the aqueous sodiumhydroxide and finally the oil is stirred into the mixture.

EXAMPLE 11

Cream Bath

| | Parts by weight |
|---|---|
| Coco fatty acid amide-$(EO)_6-CH_2COOH$ | 10 |
| Lauric acid-polydialkylolamide | 6 |
| Polyethyleneglycol-6-decanoic/octanoic acid-glyceride | 10 |
| Adduct of oleyl alcohol with 10 EO | 5 |
| Decanoic/octanoic acid-triglyceride | 10 |
| Cetyl-olyl alcohol | 16 |
| Paraffin oil | 25 |
| Corn germ oil | 10 |
| Distilled lanoline alcohol | 8 |

Preparation: The first above-mentioned four components (the surfactants) are mixed with heating at about 50° C. and the oils are dissolved therein at 40° C. If haziness occurs, the solution can be cleared with 1–2% of water.

EXAMPLE 12

Showering Foam Composition

|  | Parts by weight |
|---|---|
| $C_{11}H_{23}$—CONH—(EO)$_6$—CH$_2$COOH | 15 |
| 28% RO—(C$_2$H$_4$O)$_2$SO$_3$Na (vide Example 4) | 10 |
| Diethanolamide of coco fatty acid | 5 |
| Sodium salt of fatty acid tauride (50%) | 10 |
| Oxyethylated lanoline alcohol (16 EO) | 5 |
| 1,3-Butyleneglycol | 5 |
| Water | to 100 |
| Triethanolamine | q.s. |

Preparation: The first five components are stirred into water in the indicated sequence, then butyleneglycol is added and finally the pH is adjusted at 6.9 with triethanolamine.

EXAMPLE 13

Cream for Normal or Dry Skin

| | |
|---|---|
| $C_{17}H_{35}$—CO—NH—(C$_2$H$_4$O)$_8$—CH$_2$COOH | 5 g |
| $C_{17}H_{35}$—CO—NH—C$_2$H$_4$O—CH$_2$COOH | 2 g |
| Corn germ oil | 10 g |
| Acetylan (acetylated lanoline alcohol) | 2 g |
| Cetylalcohol | 5 g |
| Oleyl alcohol | 8 g |
| MgCl$_2$ | 0.5 g |
| Glycerol | 4 g |
| Triethanolamine | 1.63 g |
| Water | to 100 |
| Preservative | 0.08% |

The first six ingredients which form the oil phase are mixed and heated to 65°-70° C. The MgCl$_2$, glycerol and water are separately mixed and heated at the same temperature and thereafter slowly added to the oil phase with stirring. After complete emulsification the triethanolamine which serves as neutralizing agent is added. Then the entire mixture is further stirred at 40° C. and finally the preservative is added at this temperature.

EXAMPLE 14

Creams for Fatty Skins

| | A | B |
|---|---|---|
| $C_{17}H_{35}$—CO—NH—(EO)$_8$—CH$_2$COOH | 3 g | 5 g |
| $C_{17}H_{35}$—CO—NH—C$_2$H$_4$O—CH$_2$COOH | 1 g | 2 g |
| Isopropylmyristate | 10 g | 6 g |
| Acetulan | 2 g | 6 g |
| Cetyl alcohol | 5 g | 5 g |
| Aleyl alcohol | 8 g | 8 g |
| Glycerol monostearate | 3 g | — |
| MgCl$_2$ | 0.5 g | 0.5 g |
| Glycerol | 4 g | 4 g |
| Triethanolamine | 1.23 g | 1.23 g |
| Water | to 100 | to 100 |
| Preservative | 0.08% | 0.08% |

The preparation is carried out in the same way as in Example 7. In composition (A) the glycerol monostearate also belongs to the fatty phase.

What is claimed is:

1. In a composition for prolonged or multiple contact with the human skin and containing a detergent agent, the improvement wherein said detergent agent consists essentially of at least one detergent selected from the group consisting of compounds of the formula:

R—CO—NH—(C$_2$H$_4$O)$_n$—CH$_2$COOH, wherein R—CO— is the residue of at least one aliphatic carboxylic acid of 6-22 carbon atoms and n represents a number having an average value of 2-10, as well as their salts with alkali metals, ammonium and amines, and at least a carrier therefor.

2. Composition according to claim 1, wherein n is at least 3.

3. Composition according to claim 1, wherein R—CO— represents the residue of lauric acid.

4. Composition according to claim 1, wherein R—CO— represents the residue of stearic acid.

5. Composition according to claim 1, wherein R—CO— represents the residue of coco fatty acid.

6. A composition according to claim 1 further comprising at least one of glycol, alcohol, glycerol or an ethanolamine.

7. A composition according to claim 1 comprising at least one of glycol, alcohol, glycerol or an ethanolamine.

8. A composition according to claim 7 further comprising an amount of dye only sufficient to provide said composition with color.

9. A composition according to claim 1 further comprising an amount sufficient of perfume to provide a pleasant odor.

10. A composition according to claim 9 in the form of a shampoo.

11. A composition according to claim 9 in the form of a bubble bath composition.

12. In a method involving substantial contact of human skin with a detergent composition, comprising the step of bringing the detergent composition into contact with the skin repeatedly or for a prolonged period of contact, the improvement comprising reducing secondary toxicity by using as a said detergent a compound of the formula:

R—CO—NH—(C$_2$H$_4$O)$_n$—CH$_2$COOH, wherein R—CO— is the residue of at least one aliphatic carboxylic acid of 6-22 carbon atoms and n represents a number having an average value of 2-10, as well as their salts with alkali metals, ammonium and amines.

13. In a composition in the form of a cosmetic cream, for prolonged on multiple contact with the human skin and containing a detergent agent, the improvement wherein said detergent agent consists essentially of at least one detergent selected from the group consisting of compounds of the formula:

R—CO—NH—(C$_2$H$_4$O)$_n$—CH$_2$COOH, wherein R—CO— is the residue of at least one aliphatic carboxylic acid of 6-22 carbon atoms and n represents a number having an average value of 2-10, as well as their salts with alkali metals, ammonium and amines, and at least a carrier therefor.

* * * * *

UNITED STATES PATENT AND TRADEMARK OFFICE
CERTIFICATE OF CORRECTION

PATENT NO. : 4,818,440
DATED : April 4, 1989
INVENTOR(S) : SCHAFER et al.

It is certified that error appears in the above-identified patent and that said Letters Patent is hereby corrected as shown below:

| | |
|---|---|
| Column 3, line 6 | Delete "cultures", insert therefor -- cultured -- |
| Column 3, line 21 | Delete "continued", insert therefor -- continue -- |
| Column 3, line 32 | Delete "$C_{17}H_{35}$", insert therefor -- $C_{11}H_{23}$ -- |
| Column 3, line 58 | Delete "invetion", insert therefor -- invention -- |
| Column 5 | Under EXAMPLE 5, Delete "diethyanolamide", insert therefor -- diethanolamide -- |

On the face of the patent:

Assignee: Delete "Bodegraven", insert therefor -- Geleen --

Signed and Sealed this

Twenty-sixth Day of November, 1991

Attest:

HARRY F. MANBECK, JR.

*Attesting Officer*  *Commissioner of Patents and Trademarks*